(12) United States Patent
Lin et al.

(10) Patent No.: US 11,324,782 B2
(45) Date of Patent: May 10, 2022

(54) METHOD OF PREVENTING OBESITY USING HERB FERMENT (71) Applicant: TCI CO., LTD, Taipei (TW)

(72) Inventors: Yung-Hsiang Lin, Taipei (TW); Wei-Hsiu Chuang, Taipei (TW)

(73) Assignee: TCI CO., LTD., Taipei (TW)

( * ) Notice: Subject to any disclaimer, the term of this patent is extended or adjusted under 35 U.S.C. 154(b) by 256 days.

(21) Appl. No.: 16/727,164

(22) Filed: Dec. 26, 2019

(65) Prior Publication Data
US 2021/0196764 A1 Jul. 1, 2021

(51) Int. Cl.
A61K 35/74 (2015.01)
A61P 3/04 (2006.01)
A61K 36/185 (2006.01)
C12R 1/865 (2006.01)
C12R 1/25 (2006.01)

(52) U.S. Cl.
CPC ............ *A61K 35/74* (2013.01); *A61K 36/185* (2013.01); *A61P 3/04* (2018.01); *C12R 2001/25* (2021.05); *C12R 2001/865* (2021.05)

(58) Field of Classification Search
CPC ...... A61K 35/74; A61K 36/185; A61K 35/00; A61K 2236/19; A61P 3/04
See application file for complete search history.

(56) References Cited

PUBLICATIONS

Fan et al., Mol. Nutr. Food Res., 2013, vol. 57, p. 2075-2078, and 7 pages of Supporting Material. DOI 10.1002/mnfr.201300054.*

* cited by examiner

*Primary Examiner* — Kade Ariani
(74) *Attorney, Agent, or Firm* — Chieh-Mei Wang (57) ABSTRACT The present invention provides a use of herb ferment for preparing a composition for preventing and/or treating obesity; wherein, the herb is *Abelmoschus esculentus*. The fermentation process of the present invention can enhance the content of total polysaccharide in the herb ferment, and effectively increase the amylase inhibition rate and the glucosidase inhibition rate of the herb ferment to effectively inhibit the decomposition and absorption of starch and glucoside. The herb ferment of the present invention can also effectively reduce the blood glucose of subjects after meals, and can effectively reduce the body weight, BMI value, waist circumference, visceral fat, average whole body fat percentage, and average body fat percentage, and can be effectively used to regulate blood glucose and blood lipids for weight loss. The herb ferment is prepared by fermenting the herb extract to yeast and lactic acid bacteria.

10 Claims, 5 Drawing Sheets

METHOD OF PREVENTING OBESITY USING HERB FERMENT

BACKGROUND OF THE INVENTION

1. Field of the Invention

The present invention relates to a method of preventing and/or treating obesity using herb ferment, and particularly to the method of preventing and/or treating obesity using *Abelmoschus esculentus* ferment, and more particularly to the method of preventing and/or treating obesity using the *Abelmoschus esculentus* ferment which is prepared by using the *Abelmoschus esculentus* extract by the fermentation process of the present invention.

2. The Prior Art

In recent years, the incidence of global obesity has gradually increased. The World Health Organization (WHO) described "rapid disease" as a rapidly spreading obesity and called it "Globesity." According to a 2014 World Health Organization estimate, about 39% of the population in the world is overweight (about 1.9 billion people) and 13% is obese (about 600 million people). With the changes in eating habits and the improvement of quality of life, the prevalence of obesity in Taiwan has also increased year by year. According to the survey on the changes in national nutrition and health status announced by the National Health Promotion Administration, Ministry of Health and Welfare, Taiwan, the prevalence rate of overweight or obesity in adults is as high as 43%; wherein, the ratio of male and female is 49% and 40% respectively. That is, every two men in Taiwan get one overweight or obese and every two to three women get one overweight or obese, and more than 200,000 of them have reached the standard of morbid obesity which must be treated with surgery.

Obese individuals increase the risk of a variety of health problems and could lead to a variety of complications, including hypertension, hyperlipidemia, cardiovascular disease, sleep apnea, stenosis, degenerative arthritis, and hyperuricemia Inflammation, type-2 diabetes, and cancer. Among them, if there are too many fat cells in the body, it would secrete harmful substances that hinder the reaction of insulin, making the function of insulin blocked, and it would not be able to effectively regulate the rising blood glucose, which will lead to the symptoms of hyperglycemia. If the body is in a state of high blood glucose for a long time, it would make the pancreas to secrete more insulin to lower blood glucose. Once the pancreas exceeds the load, it would develop type-2 diabetes. In addition, blood lipids refer to fats in the blood, mainly including cholesterol and triglycerides. When the concentration of cholesterol or triglycerides in the blood is higher than normal, it is called hyperlipidemia; when the concentration of cholesterol or triglyceride in the blood is too high, or high-density lipoprotein in the blood is too low, also known as dyslipidemia. In addition to causing heart disease, hyperlipidemia is also closely related to chronic diseases such as stroke, hypertension, diabetes, and kidney disease.

Therefore, obesity reduces the quality of life and could lead to premature death, so the average life expectancy of patients with morbid obesity is much less than that with normal weight. Although genes might be involved in the development of obesity, the obesity epidemic is largely due to high-calorie diets and sedentary lifestyles. Therefore, lifestyle changes can prevent obesity and its complications.

Although low-calorie diets and regular exercise can be used to reduce weight and treat obesity, these methods are difficult to implement and their efficacy is limited, mainly due to adaptive physiological mechanisms that maintain energy storage in the body. In addition, some drugs have been approved for the treatment of long-term obesity (such as Orlistat, Phentermine, or Topiramate). However, these drugs often cause serious side effects, which limit the efficacy of treatment and patient compliance. Furthermore, bariatric surgery can cause significant weight loss, but this interventional surgery is not suitable for all overweight people; for these reasons, research on safe and effective ways to reduce weight and fat accumulation does have its needs.

In summary, in response to the changes in obesity and overall health problems caused by obesity while changes in living styles and eating habits, and based on the improvement of living standards and the improvement of the concept of health care, it is necessary to develop an effective method that can effectively regulate individual blood glucose and blood lipids, slow down the complications caused by obesity, and fundamentally reduce the decomposition and absorption of nutrients that lead to excessive intake of obesity, in order to reduce the formation of fat and reduce the chance of obesity.

SUMMARY OF THE INVENTION

To solve the foregoing problem, one objective of the present invention is to provide an method of preventing and/or treating obesity, comprising administering a composition comprising an effective amount of herb ferment to a subject in need thereof; wherein the herb ferment is an *Abelmoschus esculentus* ferment, and the *Abelmoschus esculentus* ferment regulates blood glucose or blood lipids of the subject.

The other objective of the present invention is to provide a herb ferment; wherein, the herb ferment is an *Abelmoschus esculentus* ferment, and the *Abelmoschus esculentus* ferment obtained by a method comprising: extracting an *Abelmoschus esculentus* with a solvent to obtain an *Abelmoschus esculentus* extract; fermenting a *Saccharomyces cerevisiae* and a *Lactobacillus plantarum* simultaneously in the *Abelmoschus esculentus* extract; and separating the *Abelmoschus esculentus* ferment.

The other objective of the present invention is to provide a method of preparation of an *Abelmoschus esculentus* ferment, comprising: extracting an *Abelmoschus esculentus* with a solvent to obtain an *Abelmoschus esculentus* extract; fermenting a *Saccharomyces cerevisiae* and a *Lactobacillus plantarum* in the *Abelmoschus esculentus* extract; and separating the *Abelmoschus esculentus* ferment.

In one embodiment of the present invention, the *Abelmoschus esculentus* ferment inhibits absorption of starch or glucose of the subject; and the *Abelmoschus esculentus* ferment inhibits activity of an amylase or a glucosidase in the subject.

In one embodiment of the present invention, the concentration of the *Abelmoschus esculentus* ferment in the composition is at least 5% (v/v).

In one embodiment of the present invention, the *Abelmoschus esculentus* ferment reduces the body weight, body mass index value, waist circumference, visceral fat, average whole-body fat percentage, or average body fat percentage of the subject.

In one embodiment of the present invention, the solvent is water; the *Abelmoschus esculentus* is mixed with water with a solid-liquid ratio of 1-3:5-29; the *Saccharomyces cerevisiae* is added with 0.01-0.5% (v/v) and the *Lactobacillus plantarum* is added with 0.01-0.25% (v/v); and the fermentation time is 1-7 days.

In one embodiment of the present invention, the method for producing the *Abelmoschus esculentus* ferment enhances the content of total polysaccharide of the *Abelmoschus esculentus* ferment.

The *Abelmoschus esculentus* ferment obtained by the microbial fermentation process of simultaneously fermenting the *Abelmoschus esculentus* water extract with *Saccharomyces cerevisiae* and *Lactobacillus plantarum* can significantly enhances the content of total polysaccharide thereof and making the *Abelmoschus esculentus* ferment of the present invention can be more effectively used for regulating blood glucose and blood lipids. Besides, the fermentation process of present invention can effectively improve the inhibition rate of the amylase and the glucosidase of the *Abelmoschus esculentus* ferment of the present invention, so that the *Abelmoschus esculentus* ferment of the present invention can effectively inhibit the decomposition of starch and glucoside, and then can block the decomposition of starch and glucose from the source to inhibit absorption of starch or glucose of the subject so as to effectively prevent and/or treat obesity. The *Abelmoschus esculentus* ferment of the present invention can also effectively reduce the blood glucose value of the subject after meals so as effectively prevent and/or treat obesity. In addition, the *Abelmoschus esculentus* ferment of the present invention can effectively reduce the body weight, BMI value, waist circumference, visceral fat, average whole-body fat percentage, or average body fat percentage of the subject so as effectively prevent and/or treat obesity. Therefore, the *Abelmoschus esculentus* ferment of the present invention can be used for the preparation of a composition for regulating blood glucose and blood fat or preventing and/or treating obesity, and the composition is a pharmaceutical product, a skin care product, or a food, which can be administered to a subject in need by oral administration, smearing and the like.

The embodiments of the present invention are further described with the following drawings. The following embodiments are given to illustrate the present invention and are not intended to limit the scope of the present invention, and those having ordinary skill in the art can make some modifications and refinements without departing from the spirit and scope of the present invention. Therefore, the scope of the present invention is defined by the scope of the appended claims.

DETAILED DESCRIPTION OF THE PREFERRED EMBODIMENT

The data provided in the present invention represent approximated, experimental values that may vary within a range of ±20%, preferably ±10%, and most preferably ±5%.

Statistical analysis is performed using Excel software. Data are expressed as mean±standard deviation (SD), and the differences between these are analyzed by Student's t-test.

*Abelmoschus esculentus* is a *Malvaceae* genus and *Abelmoschus* species and one year or perennial herb plant. *Abelmoschus esculentus* is also known as yellow geranium, carob, sauerkraut, arbutin, eucalyptus, ocella, sesame, and croissant. *Abelmoschus esculentus* is native to Abyssin in the northeast of Africa, the Caribbean Sea in Egypt or tropical Asia, and was introduced to Taiwan in 1901. *Abelmoschus esculentus* is distributed in counties such as Changhua, Yunlin and Chiayi and its abundance period is from April to September every year. *Abelmoschus esculentus* plant is erect with about one-meter height. The whole plant of *Abelmoschus esculentus* is velvety; the stem of it is lignified; the flower of it is completely flower with light yellow color. After three to four days from flowers withering away, the tender fruit can be harvested. The fruit of it is a capsule and is about ten centimeters long and slender like a shofar or pepper. The peel of it is thin and leathery with a sharp tip and a light green, dark green or purple-red color. The fruit of it contains a special sticky substance, which has a special aroma or flavor and is edible and is known to have effects on improving dyspepsia and edema.

The "*Abelmoschus esculentus* ferment" describes herein is that the ferment obtains by extracting an *Abelmoschus esculentus* with a solvent to get an *Abelmoschus esculentus* extract, and then simultaneously fermenting a *Saccharomyces cerevisiae* and a *Lactobacillus plantarum* in the *Abelmoschus esculentus* extract; wherein, the solid-liquid ratio of 1-3:5-29; the *Saccharomyces cerevisiae* is added with 0.01-0.5% (v/v); the *Lactobacillus plantarum* is added with 0.01-0.25% (v/v).

The "effective concentration" or "effective amount" describes herein is that the required amount of the *Abelmoschus esculentus* ferment of the present invention for effectively improving the inhibition rate of the amylase, improving the inhibition rate of the glucosidase, reducing the blood glucose value of the subject after meals, and reducing the body weight, BMI value, waist circumference, visceral fat, average whole-body fat percentage, or average body fat percentage of the subject. The effective concentration or effective amount would vary depending on the subject to which it is administered, but the effective concentration can be determined experimentally by, for example, a dose escalation test.

According to the present invention, the operating procedures and parameter conditions for extracting are within the professional literacy and routine techniques of those having ordinary skill in the art.

According to the present invention, the operating procedures and parameter conditions for microbial fermentation are within the professional literacy and routine techniques of those having ordinary skill in the art.

According to the present invention, a pharmaceutical product can be manufactured into a form suitable for parenterally or topically administration using techniques well known to those having ordinary skill in the art, including, but not limited to, injection (for example, sterile aqueous solution or dispersion), sterile powder, external preparation, and the like.

According to the present invention, the pharmaceutical product could further comprise a pharmaceutically acceptable carrier that is widely used in pharmaceutical manufacturing techniques. For example, the pharmaceutically acceptable carrier can comprise one or more agents selected from the group consisting of a solvent, a buffer, an emulsifier, a suspending agent, a decomposer, a disintegrating agent, a dispersing agent, a binding agent, an excipient, a stabilizing agent, a chelating agent, a diluent, a gelling agent, a preservative, a wetting agent, a lubricant, an absorption delaying agent, a liposome, and the like. The selection and quantity of these reagents falls within the professional literacy and routine skills of those having ordinary skill in the art.

According to the present invention, the pharmaceutically acceptable carrier comprises a solvent selected from the group consisting of water, normal saline, phosphate buffered saline (PBS), aqueous solution containing alcohol, and combinations thereof.

According to the present invention, the pharmaceutical product can be administered by a parenteral route selected from the group consisting of subcutaneous injection, intraepidermal injection, intradermal injection and intralesional injection.

According to the present invention, the pharmaceutical product can be manufactured into an external preparation suitable for topical application to the skin using techniques well known to those having ordinary skill in the art, including, but not limited to, an emulsions, a gel, an ointment, a cream, a patch, a liniment, a powder, an aerosol, a spray, a lotion, a serum, a paste, a foam, a drop, a suspension, a salve, and a bandage.

According to the present invention, the external preparation is prepared by mixing the pharmaceutical product of the present invention with a base which is well known to those having ordinary skill in the art.

According to the invention, the substrate could comprise one or more additives selected from the group consisting of water, an alcohol, a glycol, a hydrocarbon [such as petroleum jelly, and white petrolatum], a wax [such as paraffin and yellow wax], a preserving agent, an antioxidant, a surfactant, an absorption enhancers, a stabilizing agent, a gelling agent [such as carbopol® 974P, microcrystalline cellulose, and carboxymethylcellulose], an active agent, a humectant, an odor absorber, a fragrance, a pH adjusting agent, a chelating agent, an emulsifier, an occlusive agent, an emollient, a thickener, a solubilizing agent, a penetration enhancer, an anti-irritant, a colorant, a propellant, and the like. The selection and quantity of these additives falls within the professionalism and routine technology of those having ordinary skill in the art.

According to the invention, the skin care product can further comprise an acceptable adjuvant that is widely used in the care product manufacturing technology. For example, the acceptable adjuvant could comprise one or more agents selected from the group consisting of a solvent, a gelling agent, an active agent, a preservative, an antioxidant, a screening agent, a chelating agent, a surfactant, a dyeing agent, a coloring agent, a thickening agent, a filler, a fragrance, and an odor absorbent. The selection and quantity of these reagents falls within the professionalism and routine technology of those having ordinary skill in the art.

According to the present invention, the skin care product can be manufactured into a form suitable for skincare or makeup using techniques well known to those having ordinary skill in the art, including, but not limited to, an aqueous solution, an aqueous-alcohol solution or an oily solution, an oil-in-water type, a water-in-oil type or a composite type emulsion gel, ointment, cream, mask, patch, pack, liniment, powder, aerosol, spray, lotion, slurry, past, foam, dispersion, drop, mousse, sunblock, tonic water, foundation, makeup remover product, soap, and other body cleansing product.

According to the present invention, the skin care product could also be used in combination with one or more external use agents selected from the following activities: a whitening agent [such as tretinoin, catechin, citric acid, arbutin and vitamin C], a moisturizer, an anti-inflammatory agent, a bactericide, an ultraviolet absorber, a plant extract [such as aloe extract], a skin nutrient, an anesthetic, an anti-acne agent, an antipruritic, an analgesic, an antidermatitis agent, an antihyperkeratolytic agent, an anti-dry skin agent, an antipsoriatic agent, an antiaging agent, an antiwrinkle agent, an antiseborborheic agent, a wound-healing agent, a corticosteroid, and a hormone. The selection and quantity of these external preparations falls within the professionalism and routine technology of those having ordinary skill in the art.

According to the present invention, the food product can be used as a food additive, added by the conventional method in the preparation of the raw material, or added during the production of the food, and matched with any edible material to be made into food products for human and non-human animals.

According to the present invention, the types of the food products include, but are not limited to, beverages, fermented foods, bakery products, health foods, and dietary supplements.

The "*Saccharomyces cerevisiae*" and "*Lactobacillus plantarum*" describe herein are that respectively available stains of *Saccharomyces cerevisiae* and *Lactobacillus plantarum* for those having ordinary skill in the art. For example, the *Saccharomyces cerevisiae* and the *Lactobacillus plantarum* strain can be purchased from domestic or foreign depository institutions, or isolated and purified from natural sources by a microorganism separation method conventionally used in the art.

The present invention provides a method of preventing and/or treating obesity using herb ferment, comprising administering to a subject in need thereof a composition composted of an effective amount of the *Abelmoschus esculentus* ferment. The *Abelmoschus esculentus* ferment of the present invention is obtained by extracting *Abelmoschus esculentus* with the solid-liquid ratio of 1-3:5-29 for a specific time and temperature to get an *Abelmoschus esculentus* extract, and then simultaneously fermenting a *Saccharomyces cerevisiae* and a *Lactobacillus plantarum* in the *Abelmoschus esculentus* extract. The microbial fermentation process of the present invention can significantly enhance the content of total polysaccharide in the *Abelmoschus esculentus* ferment. The *Abelmoschus esculentus* ferment of the present invention can effectively improve the inhibition rate of the amylase, improve the inhibition rate of the glucosidase, reduce the blood glucose value of the subject after meals, and reduce the body weight, BMI value, waist circumference, visceral fat, average whole-body fat percentage, or average body fat percentage of the subject, so as to effectively prevent and/or treat obesity.

Meanwhile, the composition for preventing and/or treating obesity of the present invention could further comprise an effective amount of the *Abelmoschus esculentus* ferment of the present invention, and a pharmaceutically acceptable carrier, and the composition is a pharmaceutical product, a skin care product, or a food.

The detailed preparation method of the *Abelmoschus esculentus* ferment of the present invention, the test of the fermentation process of the present invention for improving the content of the total polysaccharide in the *Abelmoschus esculentus* ferment, the fermentation process of the present invention for improving the inhibition rate of the amylase, the fermentation process of the present invention for improving the inhibition rate of the glucosidase, the *Abelmoschus esculentus* ferment of the present invention for reducing the blood glucose value of the subject after meals, and the *Abelmoschus esculentus* ferment of the present invention for reducing the body weight, BMI value, waist circumference, visceral fat, average whole-body fat percentage, or average body fat percentage of the subject will all be described in detail below to confirm that the *Abelmoschus esculentus* ferment of the present can be effectively applied to prevent and/or treat obesity.

EXAMPLE 1

Preparation of the *Abelmoschus Esculentus* Ferment

In the embodiment of the present invention, the fruits of *Abelmoschus esculentus* in Taiwan and the solvent of water, alcohol, or alcohol-water mixture were uniformly mixed at a ratio of 1-3:5-29 (w/w); wherein, the preferably solvent was water. The mixture was simultaneously sterilized and extracted at 50-100° C. for 0.5 to 3 hours to obtain an *Abelmoschus esculentus* extract. In a preferred embodiment of the present invention, the extraction solvent was water to obtain an *Abelmoschus esculentus* water extract. The *Abelmoschus esculentus* extract was cooled to room temperature for subsequent fermentation. Next, 0.01-0.5% (w/w) of yeast (*Saccharomyces cerevisiae*, purchased from the Bioresource Collection and Research Center, Taiwan, number BCRC20271) and 0.01-0.25% (w/w) *Lactobacillus* (purchased from the Bioresource Collection and Research Center, Taiwan, number BCRC910760) were simultaneously implanted into the *Abelmoschus esculentus* extract at 25-35° C. for 1-7 days fermentation, and the actual time varies depending on the state of fermentation. Finally, in the case that the two bacteria in the ferment were not removed, if the ferment meets the specification of sugar content ranges with 2-4°, pH<4, alcohol>5%, etc., the fermentation was completed and obtain the crude ferment. Then, the ferment was concentrated under reduced pressure at 45-70° C., and filtered through a 200-400 mesh sieve, and then 40-70% isomalto-oligosaccharide was added to adjust the specifications and then sterilized to obtain the *Abelmoschus esculentus* ferment of the present invention.

EXAMPLE 2

Effect of the *Abelmoschus Esculentus* Ferment on Increasing the Total Content of the Polysaccharide In the embodiment of the present invention, in order to test the fermentation process increasing the total content of the polysaccharide in the *Abelmoschus esculentus* ferment of the present invention, the Phenol-sulfuric acid assay was used to quantify the concentration of total polysaccharide in samples. When the sugar encounters a strong acid, the structural hydroxyl group would combine with the phenol and produce an orange liquid, so the colorimetric method (in particular, the absorbance of the sample at 490 nm) could be used to detect the concentration of the total polysaccharide therein. First, 10 mg of D-Glucose (purchased from JT Baker, USA, number 1916-01) was placed in a 10 mL volumetric flask, and ddH$_2$O was added to bring the total volume to 10 mL to obtain the D-Glucose stock solution (1 mg/mL). Then, the serially dilute of D-Glucose stock solution was series diluted as the formulation showing in Tablet, which was diluted with ddH$_2$O into 0 μg/mL, 20 μg/mL, 50 μg/mL, 100 μg/mL, 150 μg/mL, and 200 μg/mL of the D-Glucose solutions. Separately, 1.25 g of Phenol (purchased from Merck, Germany, number 1.00206.0250) was placed in a volumetric flask, and ddH$_2$O was further added to bring the total volume to 25 mL to complete a 5% Phenol working solution.

TABLE 1

The formulation for series diluting the D-Glucose stock solution

| | Concentration (μg/mL) | | | | | |
|---|---|---|---|---|---|---|
| | 0 | 20 | 50 | 100 | 150 | 200 |
| Glucose stock | 0 μL | 20 μL | 50 μL | 100 μL | 150 μL | 200 μL |
| ddH$_2$O | 1000 μL | 980 μL | 950 μL | 900 μL | 850 μL | 800 μL |

Then, the regression curve of the standard solution was drawn. 100 μL of the standard solution of each concentration was placed in a glass test tube, and 500 μL of 5% Phenol working solution was added into each tube, and the 2.5 mL of sulfuric acid solution (95.5% of H$_2$SO$_4$, purchased from Showa, Japan, No. 1970-5250) was slowly added into each tube. The mixture was uniformly mixed with Vortex and reacted for 20 minutes. Next, 200 μL of each mixture was placed in a 96-well culture plate, and the absorbance at 490 nm was measured to draw a regression curve formula for standard solutions. Then, 100 μL of the *Abelmoschus esculentus* water extract (see EXAMPLE 1) and the *Abelmoschus esculentus* ferment of the present invention were respectively added into a glass test tube, and 500 μL of 5% Phenol solution was added into each tube, and 2.5 mL of sulfuric acid solution was also slowly added into each tube. The mixture was uniformly mixed with Vortex and reacted for 20 minutes. Next, 200 μL of each mixture was placed in a 96-well culture plate, and the absorbance at 490 nm was measured, and the interpolation was used to calculates the concentration of dilutes samples by the above regression curve formula for the standard solutions, and then multiplies the dilution factor to obtain the actual concentration of the total polysaccharide in the original *Abelmoschus esculentus* water extract and the *Abelmoschus esculentus* ferment of the present invention.

Figure 1:
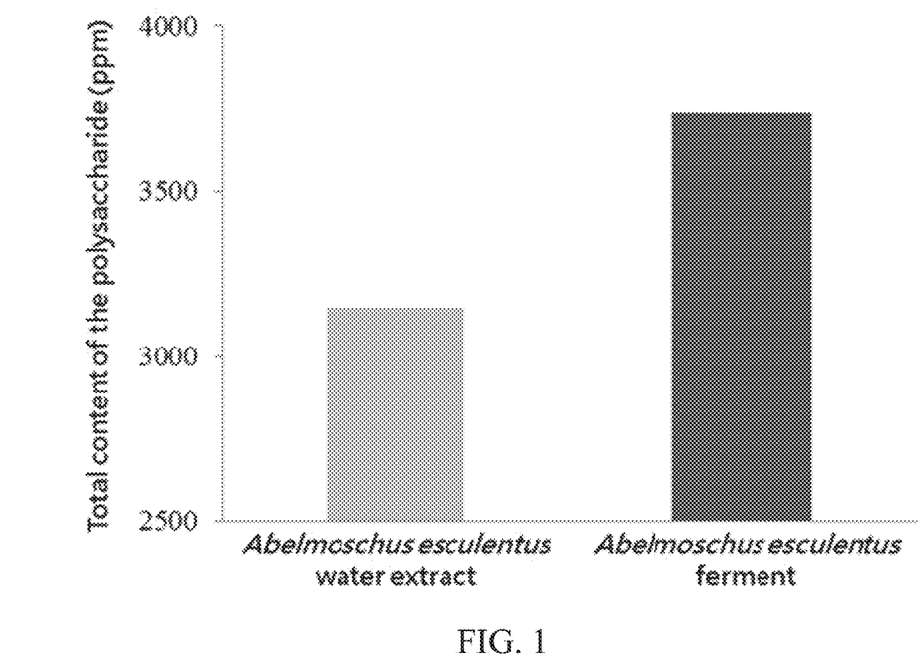
FIG. 1 shows a bar graph that the *Abelmoschus esculentus* ferment increases the total content of the polysaccharide itself.

The results of the increasing the total content of the polysaccharide in the *Abelmoschus esculentus* ferment of the present invention were shown in FIG. 1. As showing in FIG. 1, the total content of the *Abelmoschus esculentus* water extract was 3135 ppm; however, the total content of the *Abelmoschus esculentus* ferment of the present invention was 3738 ppm, which was the 1.2 times of the unfermented *Abelmoschus esculentus* water extract. The results indicate that the fermentation process of the present invention can effectively increase the total content of the polysaccharide in the *Abelmoschus esculentus* ferment of the present invention so as to make the *Abelmoschus esculentus* ferment of the present invention more effective apply to regulate blood glucose and blood lipids.

EXAMPLE 3

Effect of the *Abelmoschus Esculentus* Ferment on Inhibiting the Activity of Amylase In the embodiment of the present invention, in order to test the fermentation process increasing the ability of the *Abelmoschus esculentus* ferment of the present invention on inhibiting the activity of amylase, the characteristic that the amylase hydrolyzed starch would produce reducing sugars (e.g., glucose, maltose, etc.) was used to test the activity of amylase; wherein, the reducing sugars have a functional group of an aldehyde group (—CHO) or a ketone group (—C=O), and thus has a reducing property, which could reduce 3,5-dinitr osalicylic acid (DNS) into 3-amino-5-nitrosalicylic acid in an alkaline solution, and 3-amino-5-nitrosalicylic acid could absorb lights with 540 nm wave, and the absorbance is directly proportional to the concentration of 3-amino-5-nitrosalicylic acid. Therefore, the principle could be used to determine the relative activity or relative content of amylase in the test substance.

First, the following solutions were first prepared: 0.02 M sodium phosphate buffer (pH 6.9, and containing 6 mM sodium chloride (NaCl), hereinafter referred to as Pi buffer solution), which was that dissolved 0.7356 g of sodium hydrogen phosphate ($Na_2HPO_4$, purchased from JT Baker, USA, No. 3828-01), 0.5492 g of sodium dihydrogen phosphate ($NaH_2PO_4$, purchased from Sigma, USA, No. 04270), and 1.7532 g of sodium chloride in 500 mL of $H_2O$; 2 N sodium hydroxide solution (NaOH, purchased from Macron, USA, No. 7708-10), which was that dissolved 8 g of hydroxide in 100 mL of $H_2O$; 1 g of 3,5-dinitrosalicylic acid (purchased from Sigma, USA, number D0550) was dissolved in 50 mL of deionized $H_2O$ and slowly added 30 g sodium potassium tartrate tetrahydrate (purchased from Sigma, USA, No. 32312), and then slowly added 20 mL of 2 N sodium hydroxide, and finally deionized $H_2O$ was added to bring the total volume to 100 mL to obtain the dinitrosalicylic acid color reagent, which was the terminator of the reaction, and the storage life was two weeks; 1 g of starch (purchased from Sigma, USA, No. 59765) was dissolved in 100 mL of Pi buffer solution, and slowly heated to make it complete dissolution, and then was reduced to room temperature and then $H_2O$ was added to bring the total volume to 100 mL to obtain the 1% starch solution, which was stored at 4° C., and needed to be acclimated at room temperature for at least 4 to 5 minutes before using it; and 0.996 g α-amylase (purchased from sigma, USA, No. A3176, stored at 4° C.) was dissolved in 25 mL of Pi buffer solution to obtain 5 units/mL of α-amylase solution, which could be stored for 2-3 days at 4° C.

The following experimental group was used as the 10th minute final group: first, 200 μL of the same diluted ratio of the *Abelmoschus esculentus* water extract (see Example 1) and the *Abelmoschus esculentus* ferment of the present invention were separately added into new micro-tubes, and each group was performed three repetitions. Next, 200 μL of 5 units/mL α-amylase solution dissolved in Pi buffer solution was added into each tube, then evenly mixed with Vortex and was reacted at 25° C. for 10 minutes. 200 μL of 1% starch solution was then added into each tube, then evenly mixed with Vortex, and was reacted at 25° C. for 10 minutes. 400 μL of reaction terminator was added into each tube, i.e. the dinitrosalicylic acid color reagent, then evenly mixed with Vortex and then was reacted in boiling water for 5 minutes, then cooled to room temperature. Each reaction solution was diluted into appropriate the range for detecting absorbance with $H_2O$; for example, 150 μL of the reaction solution was added with 850 μL of $H_2O$. Finally, 200 μL of each diluted reaction solution was taken into a 96-well culture plate, and the absorbance at 540 nm was measured; wherein, the group added with 200 μL of Pi buffer solution was used as a control group.

The following experimental group was used as the 0th minute starting group: first, 200 μL of the same diluted ratio of the *Abelmoschus esculentus* water extract (see Example 1) and the *Abelmoschus esculentus* ferment of the present invention were separately added into new micro-tubes. Next, 200 μL of 5 units/mL α-amylase solution dissolved in Pi buffer solution was added into each tube, then evenly mixed with Vortex and was reacted at 25° C. for 10 minutes. In order to prevent the α-amylase from continually reacted, 400 μL of reaction terminator was necessary to be added into each tube, then evenly mixed with Vortex and then was reacted in boiling water for 5 minutes, then cooled to room temperature. Then, 200 μL of 1% starch solution was added into each tube, then evenly mixed with Vortex, and was reacted at 25° C. for 10 minutes; wherein, because time is a key factor, the interval of addition must be properly controlled. Each reaction solution was diluted into appropriate the range for detecting absorbance with $H_2O$. Finally, 200 μL of each diluted reaction solution was taken into a 96-well culture plate, and the absorbance at 540 nm was measured; wherein, the group added with 200 μL of Pi buffer solution was used as a control group.

Figure 2:
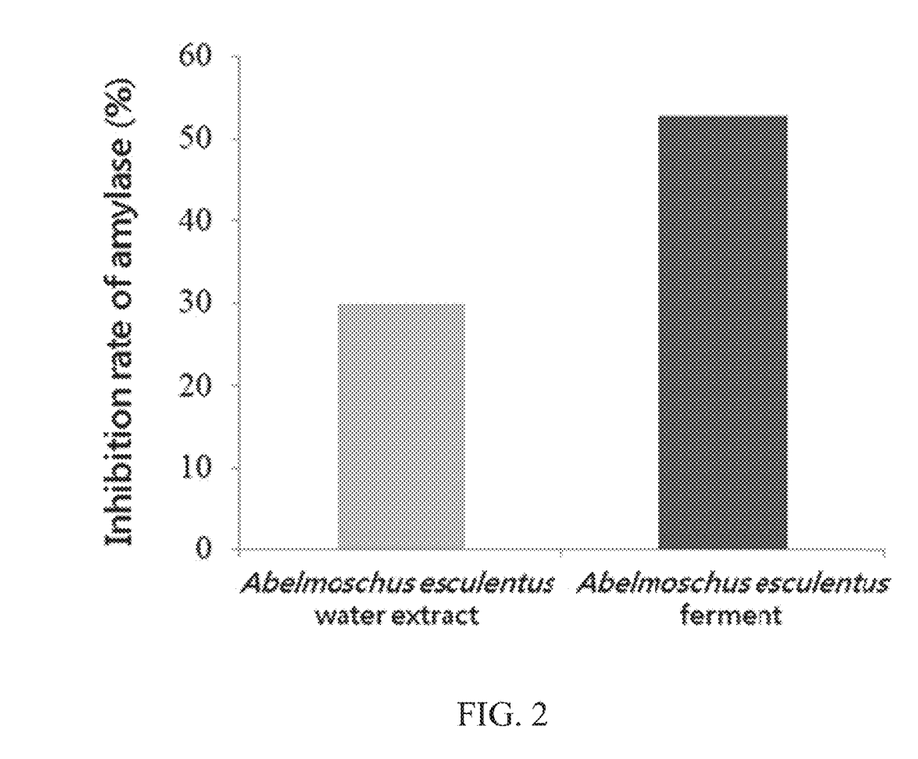
FIG. 2 shows a bar graph that the *Abelmoschus esculentus* ferment increases the inhibition rate of amylase.

The inhibition rate of amylase in the *Abelmoschus esculentus* water extract and the *Abelmoschus esculentus* fermented product of the present invention were respectively calculated by the following formula as a standard for the effect of inhibiting the activity of amylase:

$$\left[1 - \frac{A_{540nm}(Sample_{10min} - Sample_{0min})}{A_{540nm}(Control_{10min} - Control_{0min})}\right] \times 100\%$$

The results of the fermentation process increasing the ability of the *Abelmoschus esculentus* ferment of the present invention on inhibiting the activity of amylase were shown in FIG. 2. As showing in FIG. 2, the inhibition rate of amylase in the *Abelmoschus esculentus* water extract was only 29.9%; while the inhibition rate of amylase in the *Abelmoschus esculentus* ferment of the present invention was as high as 52.8%, which was 22.9% higher than that of the unfermented *Abelmoschus esculentu* water extract. The results indicate that the fermentation process of the present invention can effectively increase the inhibition rate of amylase in the *Abelmoschus esculentus* ferment of the present invention, so that the *Abelmoschus esculentus* ferment of the present invention can effectively inhibit the decomposition of starch, and can block the decomposition of starch from the source to inhibit absorption of starch of the subject so as to effectively prevent and/or treat obesity.

EXAMPLE 4

Effect of the *Abelmoschus Esculentus* Ferment on Inhibiting the Activity of Glucosidase In the embodiment of the present invention, in order to test the fermentation process increasing the ability of the

*Abelmoschus esculentus* ferment of the present invention on inhibiting the activity of glucosidase, the characteristic that the glucosidase hydrolyzed the artificial substrate p-nitrophenyl-α-D-Glucopyranoside (pNPG) and would produce glucuronic acid and p-nitrophenol, which was with yellow and could absorb lights with 405 nm wave, and the absorbance is directly proportional to the concentration of p-nitrophenol. Therefore, the principle could be used to determine the relative activity or relative content of glucosidase in the test substance.

First, the following solutions were first prepared: 0.1 M sodium phosphate buffer (pH 7.0), hereinafter referred to as Pi buffer solution, which was that dissolved 4.7283 g of sodium hydrogen phosphate and 2.0028 g of sodium dihydrogen phosphate in 400 mL of RO water, and then RO water was added to bring the total volume to 500 mL; 2.5 mM pNPG solution, which was that dissolved 0.0377 g of pNPG (purchased from Sigma, USA, number N1377) with RO water to bring the total volume to 100 mL, and then was refrigerated for 3-4 days for storage, and if the pNPG solution turns to pale yellow, the pNPG solution has been oxidized, then it needs to be reconfigured; 0.2 M sodium carbonate solution, which was that dissolved 2.1198 g of sodium carbonate ($Na_2CO_3$, purchased from Sigma, USA, No. 31432) with RO water to bring the total volume to 100 mL, and was the terminator of the reaction; 0.2 units/mL α-glucosidase (purchased from Sigma, USA, No. G5003, which contained 26 units/mg solid and there was 3.85 mg solid in total) was dissolved with 0.1 M Pi buffer solution; wherein the α-glucosidase working solution used in this example was configured in the following method: 2.0 mL of Pi buffer solution was added to the volumetric flask and 0.1 mL of purchased 50 U/mL α-glucosidase stock solution (stored at –20° C. backup), and RO water was added to bring the total volume to 25 mL to obtain the 0.2 units/mL of α-glucosidase solution.

The following experimental group was used as the 15th minute final group: first, 160 μL of the same diluted ratio of the *Abelmoschus esculentus* water extract (see Example 1) and the *Abelmoschus esculentus* ferment of the present invention were separately added into in a new 96-well culture plate, and each group was performed three repetitions. Next, 20 μL of 0.2 units/mL α-glucosidase solution dissolved in 0.1 M Pi buffer solution was added into each well, then evenly mixed and was reacted at 25° C. for 10 minutes. 20 μL of 2.5 mM pNPG solution was then added into each well, then evenly mixed and was reacted at 37° C. for 10 minutes. Next, 80 μL of reaction terminator was added into each well, then evenly mixed and the absorbance at 405 nm of each well was measured; wherein, the group added with 160 μL of Pi buffer solution was used as a control group.

The following experimental group was used as the 0th minute starting group: first, 160 μL of the same diluted ratio of the *Abelmoschus esculentus* water extract (see Example 1) and the *Abelmoschus esculentus* ferment of the present invention were separately added into in a new 96-well culture plate, and each group was performed three repetitions. Next, 20 μL of 0.1 M Pi buffer solution was added into each well, then evenly mixed and was reacted at 25° C. for 10 minutes. 20 μL of 2.5 mM pNPG solution was then added into each well, then evenly mixed and was reacted at 37° C. for 10 minutes. Next, 80 μL of reaction terminator was added into each well, then evenly mixed and the absorbance at 405 nm of each well was measured; wherein, the group added with 160 μL of Pi buffer solution was used as a control group.

Figure 3:
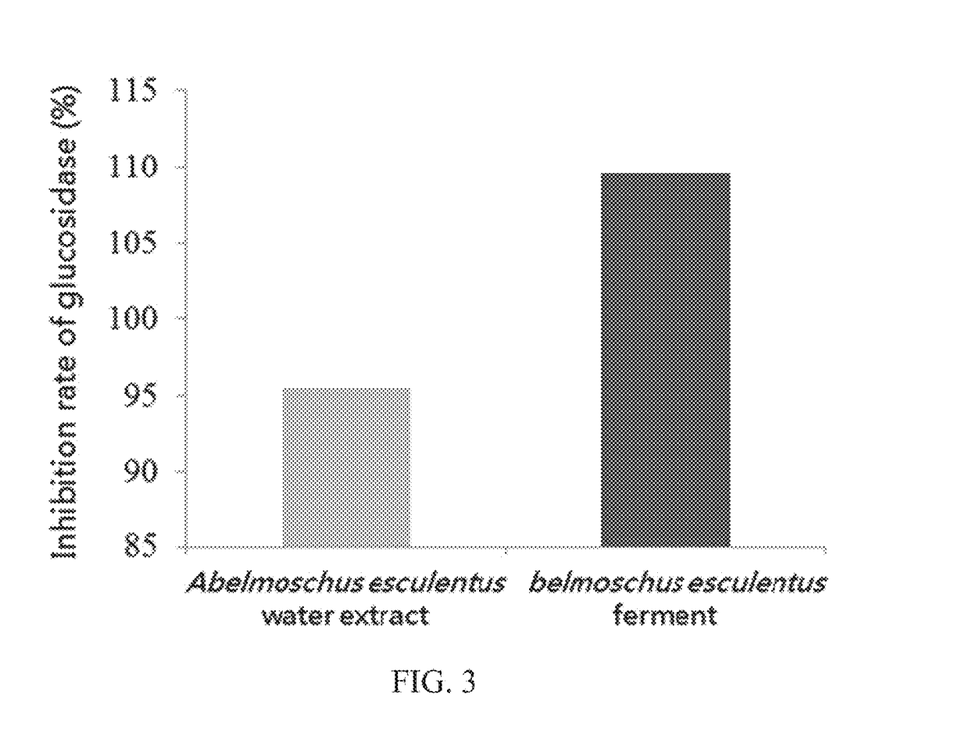
FIG. 3 shows a bar graph that the *Abelmoschus esculentus* ferment increases the inhibition rate of glucosidase.

The inhibition rate of glucosidase in the *Abelmoschus esculentus* water extract and the *Abelmoschus esculentus* fermented product of the present invention were respectively calculated by the following formula as a standard for the effect of inhibiting the activity of glucosidase:

$$\left[1 - \frac{A_{405\,nm}(Sample_{15\,min} - Sample_{0\,min})}{A_{405\,nm}(Control_{15\,min} - Control_{0\,min})}\right] \times 100\%$$

The results of the fermentation process increasing the ability of the *Abelmoschus esculentus* ferment of the present invention on inhibiting the activity of glucosidase were shown in FIG. 3. As showing in FIG. 3, the inhibition rate of glucosidase in the *Abelmoschus esculentus* water extract was only 95.5%; while the inhibition rate of glucosidase in the *Abelmoschus esculentus* ferment of the present invention was as high as 109.6%, which was 14.1% higher than that of the unfermented *Abelmoschus esculentu* water extract. The results indicate that the fermentation process of the present invention can effectively increase the inhibition rate of glucosidase in the *Abelmoschus esculentus* ferment of the present invention, so that the *Abelmoschus esculentus* ferment of the present invention can effectively inhibit the decomposition of glucoside, and can block the decomposition of glucose from the source to inhibit absorption of glucose of the subject so as to effectively prevent and/or treat obesity.

EXAMPLE 5

Effect of the *Abelmoschus Esculentus* Ferment on Reducing the Blood Glucose of Subjects After Meals In the embodiment of the present invention, in order to test the effect of the *Abelmoschus esculentus* ferment of the present invention on reducing the blood glucose of subjects after meals, the cross-test was performed. First, 7 adults were recruited as subjects and the cross-test was separated into two different days. Subjects required fasting for eight hours before the test, and blood glucose levels were measured at the start of the test as pre-meal blood glucose levels. On the first testing day, after each subject consumed three white toasts, the post-meal blood glucose levels were measured every 30 minutes, and the measurement was completed until two hours, and the result was used as the control group. Two days after the first testing day was the second testing day, and each subject also required fasting for eight hours before the test, and blood glucose levels were measured at the start of the test as pre-meal blood glucose levels. Next, each subject had a bottle of a drink containing 5-10% of the *Abelmoschus esculentus* ferment of the present invention. After fifteen minutes of drinking, each subject consumed three white toasts in ten minutes, and then the post-meal blood glucose levels were measured every 30 minutes, and the measurement was completed until two hours. Finally, the results of the two different days were compared to observe the effect of the *Abelmoschus esculentus* ferment of the present invention on reducing the blood glucose of subjects after meals.

Figure 4:
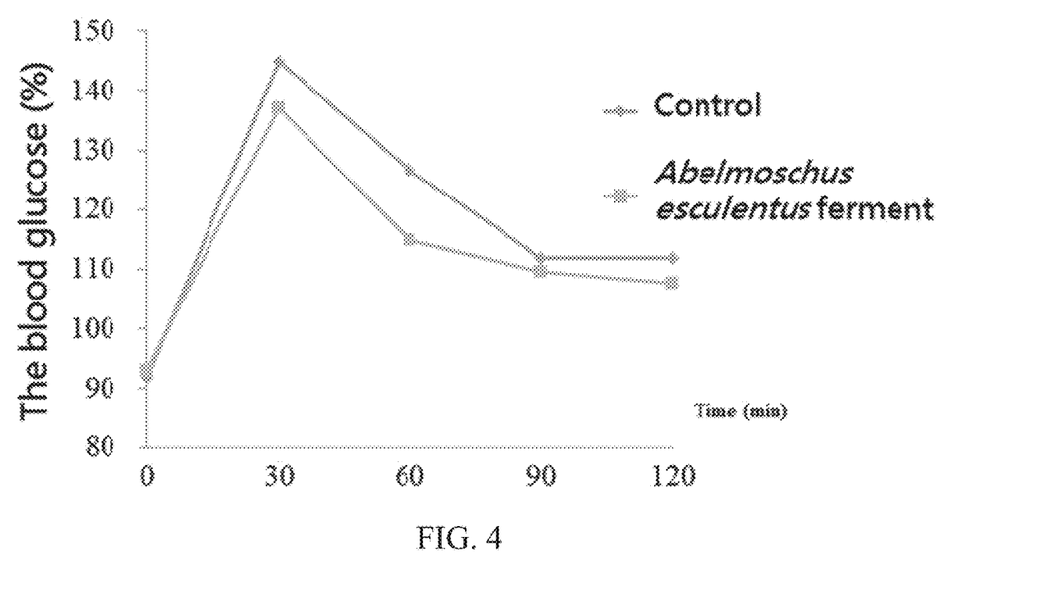
FIG. 4 shows a graph that the *Abelmoschus esculentus* ferment reduces the blood glucose of subjects after meals.

The results of the effect of the *Abelmoschus esculentus* ferment of the present invention on reducing the blood glucose of subjects after meals were shown in FIG. 4. As showing in FIG. 4, without having the *Abelmoschus esculentus* ferment of the present invention, the pre-meal blood glucose level of the subject was 93 mg/dL, and the blood glucose level of the 30th minute after consuming white toasts was 145 mg/dL, the blood glucose level of the 60th minute was 126.7 mg/dL, the blood glucose level of the 90th minute was 111.8 mg/dL, and the blood glucose level of the 120th minute was 112.0 mg/dL. While having the *Abelmoschus esculentus* ferment of the present invention, the pre-meal blood glucose level of the subject was also 93 mg/dL; however, the blood glucose level of the 30th minute after consuming white toasts was 137.1 mg/dL, the blood glucose level of the 60th minute was 114.9 mg/dL, the blood glucose level of the 90th minute was 109.6 mg/dL, and the blood glucose level of the 120th minute was 107.7 mg/dL, which was 10.4%, 14.4%, 3.9%, and 6.1% lower than that of the control group without having the *Abelmoschus esculentus* ferment of the present invention, respectively. The results indicate that the *Abelmoschus esculentus* ferment of the present invention can effectively reduce the blood glucose of subjects after meals, and can effectively regulate blood glucose so as to effectively prevent and/or treat obesity.

EXAMPLE 6

Effect of the *Abelmoschus Esculentus* Ferment on Preventing and/or Treating Obesity In the embodiment of the present invention, in order to test the effect of the *Abelmoschus esculentus* ferment on preventing and/or treating obesity, first, male or female subjects in total of ten were recruited; wherein, the subjects had the following characteristics: BMI≥24, body fat of males>25%, body fat of female>30%, high fasting blood glucose levels but not diabetic patients, and none of them was taking the medicines for controlling blood glucose. The ten subjects had had a bottle of a drink containing 5-10% of the *Abelmoschus esculentus* ferment of the present invention before the daily meal, and the body weight index, including body weight, body mass index (BMI) value, waist circumference, visceral fat, average whole-body fat percentage, and average body fat percentage, of the subjects were determined before and two weeks after having the *Abelmoschus esculentus* ferment.

Figure 5:
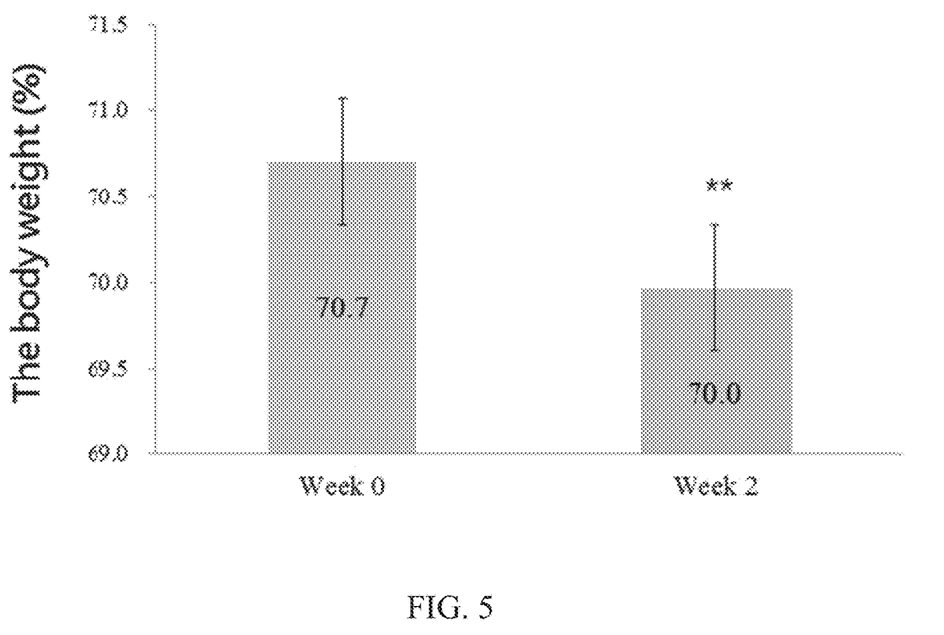
FIG. 5 shows a bar graph that the *Abelmoschus esculentus* ferment reduces the body weight of subjects. ** $p<0.01$.

The results of the effect of the *Abelmoschus esculentus* ferment of the present invention on reducing the body weight of subjects were shown in FIG. 5. As showing in FIG. 5, before having the *Abelmoschus esculentus* ferment of the present invention, the average body weight of the subjects was 70.7 kg; and after having the *Abelmoschus esculentus* ferment of the present invention for two weeks, the average body weight of the subjects was significantly reduced to 70 kg, which was 0.7 kg significantly lower than that before having the *Abelmoschus esculentus* ferment of the present invention. The results indicate that the *Abelmoschus esculentus* ferment of the present invention can effectively reduce the body weight of subjects to effectively prevent and/or treat obesity.

Figure 6:
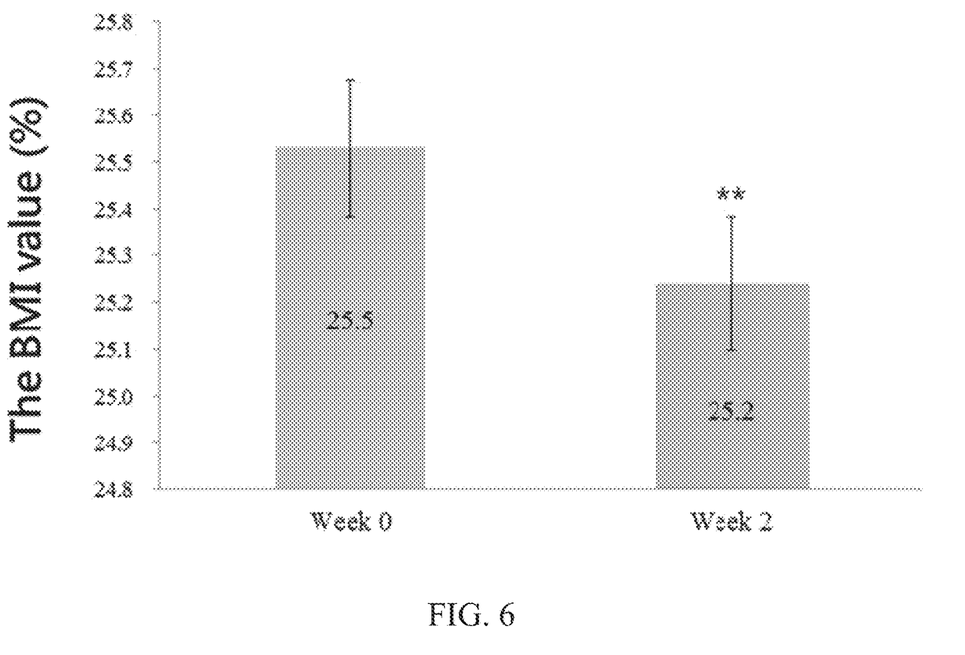
FIG. 6 shows a bar graph that the *Abelmoschus esculentus* ferment reduces the BMI value of subjects. ** $p<0.01$.

The results of the effect of the *Abelmoschus esculentus* ferment of the present invention on reducing the BMI value of subjects were shown in FIG. 6. As showing in FIG. 6, before having the *Abelmoschus esculentus* ferment of the present invention, the average BMI value of the subjects was 25.5; and after having the *Abelmoschus esculentus* ferment of the present invention for two weeks, the average BMI value of the subjects was significantly reduced to 25.2, which was 0.3 significantly lower than that before having the *Abelmoschus esculentus* ferment of the present invention. The results indicate that the *Abelmoschus esculentus* ferment of the present invention can effectively reduce the BMI value of subjects to effectively prevent and/or treat obesity.

Figure 7:
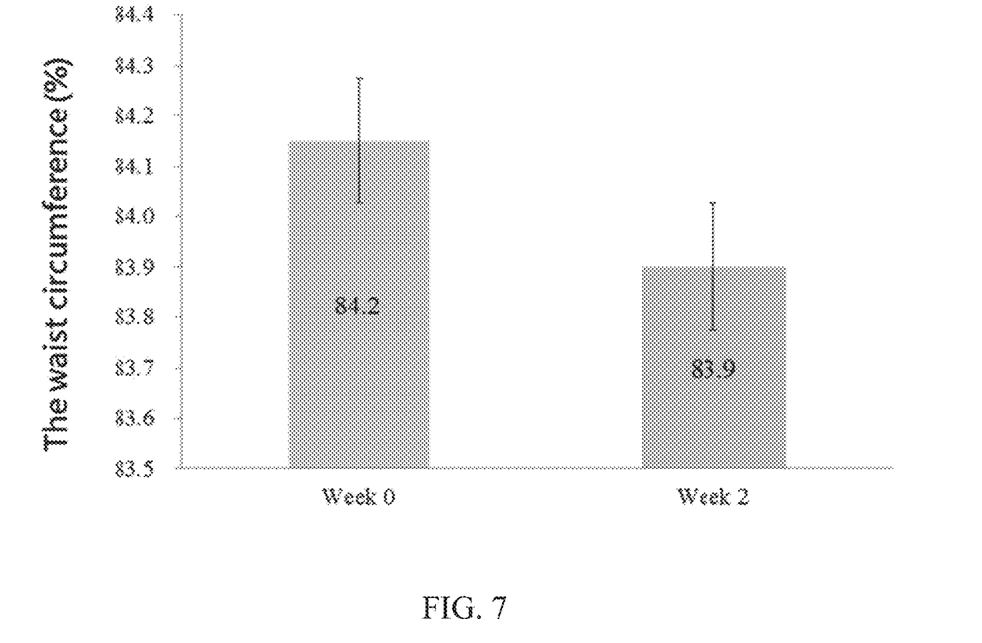
FIG. 7 shows a bar graph that the *Abelmoschus esculentus* ferment reduces the waist circumference of subjects.

The results of the effect of the *Abelmoschus esculentus* ferment of the present invention on reducing the waist circumference of subjects were shown in FIG. 7. As showing in FIG. 7, before having the *Abelmoschus esculentus* ferment of the present invention, the average waist circumference of the subjects was 84.2 cm; and after having the *Abelmoschus esculentus* ferment of the present invention for two weeks, the average waist circumference of the subjects was significantly reduced to 83.9 cm, which was 0.3 cm significantly lower than that before having the *Abelmoschus esculentus* ferment of the present invention. The results indicate that the *Abelmoschus esculentus* ferment of the present invention can effectively reduce the waist circumference of subjects to effectively prevent and/or treat obesity.

Figure 8:
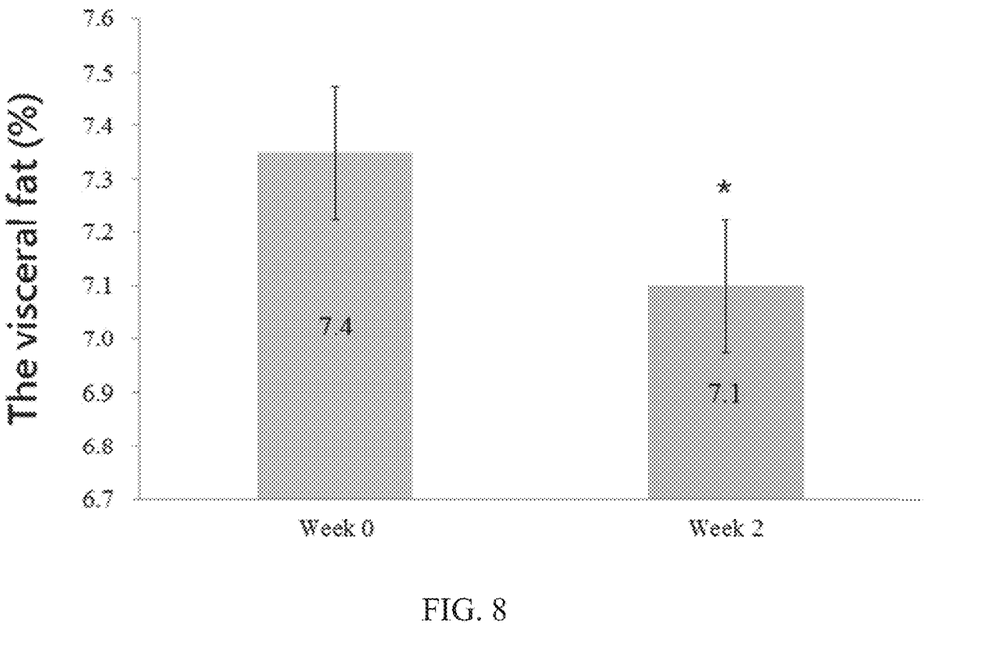
FIG. 8 shows a bar graph that the *Abelmoschus esculentus* ferment reduces the visceral fat of subjects. * $p<0.05$.

The results of the effect of the *Abelmoschus esculentus* ferment of the present invention on reducing the visceral fat of subjects were shown in FIG. 8. As showing in FIG. 8, before having the *Abelmoschus esculentus* ferment of the present invention, the average visceral fat of the subjects was 7.4; and after having the *Abelmoschus esculentus* ferment of the present invention for two weeks, the average visceral fat of the subjects was significantly reduced to 7.1, which was 0.3 significantly lower than that before having the *Abelmoschus esculentus* ferment of the present invention. The results indicate that the *Abelmoschus esculentus* ferment of the present invention can effectively reduce the visceral fat of subjects to effectively prevent and/or treat obesity.

Figure 9:
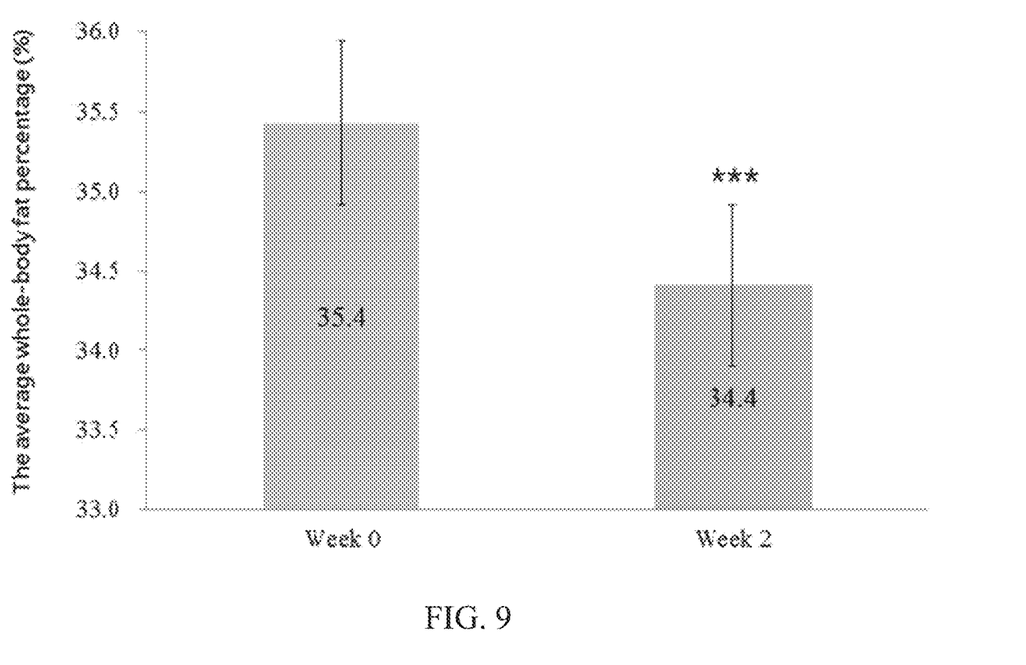
FIG. 9 shows a bar graph that the *Abelmoschus esculentus* ferment reduces the average whole-body fat percentage of subjects. *** $p<0.001$.

The results of the effect of the *Abelmoschus esculentus* ferment of the present invention on reducing the average whole-body fat percentage of subjects were shown in FIG. 9. As showing in FIG. 9, before having the *Abelmoschus esculentus* ferment of the present invention, the average whole-body fat percentage of the subjects was 35.4%; and after having the *Abelmoschus esculentus* ferment of the present invention for two weeks, the average whole-body fat percentage of the subjects was significantly reduced to 34.4%, which was 1% significantly lower than that before having the *Abelmoschus esculentus* ferment of the present invention. The results indicate that the *Abelmoschus esculentus* ferment of the present invention can effectively reduce the average whole-body fat percentage of subjects to effectively prevent and/or treat obesity.

Figure 10:
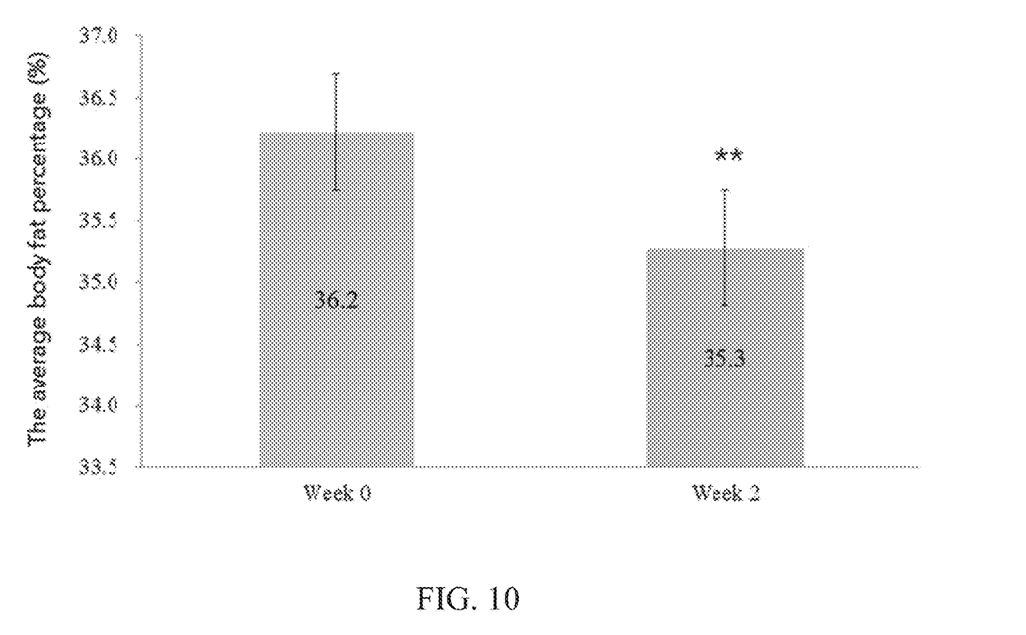
FIG. 10 shows a bar graph that the *Abelmoschus esculentus* ferment reduces the average body fat percentage of subjects. ** $p<0.01$.

The results of the effect of the *Abelmoschus esculentus* ferment of the present invention on reducing the average body fat percentage of subjects were shown in FIG. 10. As showing in FIG. 10, before having the *Abelmoschus esculentus* ferment of the present invention, the average body fat percentage of the subjects was 36.2%; and after having the *Abelmoschus esculentus* ferment of the present invention for two weeks, the average body fat percentage of the subjects was significantly reduced to 35.3%, which was 0.9% significantly lower than that before having the *Abelmoschus esculentus* ferment of the present invention. The results indicate that the *Abelmoschus esculentus* ferment of the present invention can effectively reduce the average body fat percentage of subjects to effectively prevent and/or treat obesity.

In summary, the *Abelmoschus esculentus* ferment obtained by the microbial fermentation process of simultaneously fermenting the *Abelmoschus esculentus* water extract with *Saccharomyces cerevisiae* and *Lactobacillus plantarum* can significantly enhances the content of total polysaccharide thereof and making the *Abelmoschus esculentus* ferment of the present invention can be more effectively used for regulating blood glucose and blood lipids. Besides, the fermentation process of present invention can effectively improve the inhibition rate of the amylase and the glucosidase of the *Abelmoschus esculentus* ferment of the present invention, so that the *Abelmoschus esculentus* ferment of the present invention can effectively inhibit the decomposition of starch and glucoside, and then can block the decomposition of starch and glucose from the source to inhibit absorption of starch or glucose of the subject so as to effectively prevent and/or treat obesity. The *Abelmoschus esculentus* ferment of the present invention can also effectively reduce the blood glucose value of the subject after meals so as to effectively prevent and/or treat obesity. In addition, the *Abelmoschus esculentus* ferment of the present invention can effectively reduce the body weight, BMI value, waist circumference, visceral fat, average whole-body fat percentage, or average body fat percentage of the subject so as to effectively prevent and/or treat obesity. Therefore, the *Abelmoschus esculentus* ferment of the present invention can be used for the preparation of a composition for regulating blood glucose and blood fat or preventing and/or treating obesity, and the composition is a pharmaceutical product, a skin care product, or a food, which can be administered to a subject in need by oral administration, smearing and the like.

What is claimed is:

1. A method of preventing and/or treating obesity, comprising administering a composition comprising an effective amount of an herb ferment to a subject in need thereof, wherein the herb ferment is an *Abelmoschus esculentus* ferment obtained by the following steps:
   (i) extracting an *Abelmoschus esculentus* with a solvent of water, alcohol, or alcohol-water mixture at 50-100° C. for 0.5 to 3 hours to obtain an *Abelmoschus esculentus* extract;
   (ii) fermenting a *Saccharomyces cerevisiae* and a *Lactobacillus plantarum* simultaneously in the *Abelmoschus esculentus* extract; and
   (iii) isolating the *Abelmoschus esculentus* ferment;
   and the *Abelmoschus esculentus* ferment regulates blood glucose and blood lipids of the subject.

2. The method according to claim 1, wherein the *Abelmoschus esculentus* ferment inhibits absorption of starch or glucose of the subject.

3. The method according to claim 1, wherein the *Abelmoschus esculentus* ferment inhibits activity of an amylase or a glucosidase in the subject.

4. The method according to claim 1, wherein the concentration of the *Abelmoschus esculentus* ferment in the composition is at least 5% (v/v).

5. The method according to claim 1, wherein the *Abelmoschus esculentus* ferment reduces the body weight, body mass index value, waist circumference, visceral fat, average whole-body fat percentage, or average body fat percentage of the subject.

6. The method according to claim 1, wherein the solvent is water.

7. The method according to claim 6, wherein the *Abelmoschus esculentus* is mixed with water with a solid-liquid ratio of 1-3:5-29.

8. The method according to claim 6, wherein the *Saccharomyces cerevisiae* is added with 0.01-5% (v/v) and the *Lactobaillus plantarum* is added with 0.01-0.25% (v/v).

9. The method according to claim 6, wherein the fermentation time is 1-7 days.

10. The method according to claim 6, wherein the method enhances the content of total polysaccharide of the *Abelmoschus esculentus* ferment.

* * * * *